United States Patent
Hierold et al.

(10) Patent No.: US 11,524,936 B2
(45) Date of Patent: Dec. 13, 2022

(54) STORAGE-STABLE FORM OF 3-METHYLTHIOPROPIONALDEHYDE

(71) Applicant: Evonik Operations GmbH, Essen (DE)

(72) Inventors: Judith Hierold, Hanau (DE); Andrea Kopp, Kleinwallstadt (DE); Stephan Rautenberg, Bornheim (DE); Christian Renner, Gruendau (DE)

(73) Assignee: Evonik Operations GmbH, Essen (DE)

( * ) Notice: Subject to any disclaimer, the term of this patent is extended or adjusted under 35 U.S.C. 154(b) by 0 days.

(21) Appl. No.: 17/282,897

(22) PCT Filed: Nov. 21, 2019

(86) PCT No.: PCT/EP2019/082083
§ 371 (c)(1),
(2) Date: Apr. 5, 2021

(87) PCT Pub. No.: WO2020/104589
PCT Pub. Date: May 28, 2020

(65) Prior Publication Data
US 2021/0347732 A1    Nov. 11, 2021

(30) Foreign Application Priority Data

Nov. 21, 2018  (EP) .................... 18207569

(51) Int. Cl.
  *C07C 323/12*    (2006.01)
  *C07C 319/12*    (2006.01)
  *C07C 319/26*    (2006.01)
(52) U.S. Cl.
  CPC .......... *C07C 323/12* (2013.01); *C07C 319/12* (2013.01); *C07C 319/26* (2013.01)
(58) Field of Classification Search
  CPC .... C07C 323/12; C07C 319/12; C07C 319/26
  See application file for complete search history.

(56) References Cited

U.S. PATENT DOCUMENTS

| | | |
|---|---|---|
| 4,048,232 A | 9/1977 | Koberstein et al. |
| 2018/0179155 A1 | 6/2018 | Hierold et al. |

FOREIGN PATENT DOCUMENTS

| | | | |
|---|---|---|---|
| CN | 102399177 B | 2/2016 | |
| CN | 109665974 * | 4/2019 | .......... C07C 319/26 |
| EP | 3 339 290 A1 | 6/2018 | |
| EP | 3339290 A1 * | 6/2018 | .......... C07C 319/12 |

OTHER PUBLICATIONS

International Search Report dated Jan. 2, 2020 in PCT/EP2019/082083 filed on Nov. 21, 2019, 2 pages.
Fernandez-Garcia, C. et al., "Supporting Information for Prebiotic Synthesis of Aminooxazoline-5′-Phosphates in Water by Oxidative Phosphorylation," The Royal Society of Chemistry 2017, 2017, S1-S42, XP055583737.
Office Action dated Jul. 29, 2022, in Chinese Patent Application No. 201980062558.3, filed Nov. 21, 2019 (with English-language Translation).
*Physical Organic Chemistry 2*, edited by Gao Zhenheng, Section 2.4.6 (Dec. 31, 1983) with partial machine generated English translation.
*Organic Chemistry Experiments*, 3rd Edition, Ye Yanchun, Section 2.4.6, "Extraction and Solution Washing" (Mar. 31, 2018) with partial English translation.
*China Feed Encyclopedida*, Li Defa, ISBN 7-109-06175-2 (2001) with partial machine generated English translation.

* cited by examiner

*Primary Examiner* — Rosalynd A Keys
(74) *Attorney, Agent, or Firm* — Oblon, McClelland, Maier & Neustadt, L.L.P.

(57) ABSTRACT

A chemical compound of formula (I),

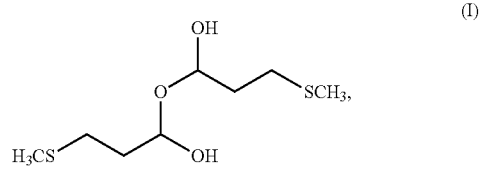

and specific compositions including 3-methylthiopropionaldehyde, 3-methylthiopropane-1,1-diol, a compound of formula I and water, and processes for producing same and also the use of same may be used for the production of 2-hydroxy-4-(methylthio)butyronitrile, methionine hydantoin, methionine. Protected forms may be used for the storage and/or transport of 3-methylthiopropionaldehyde.

16 Claims, 5 Drawing Sheets

A

Molecular weight: 104.17

B

Empirical formula: $C_4H_{10}O_2S$
Molecular weight: 122.19

C

Empirical formula: $C_8H_{18}O_3S_2$
Molecular weight: 226.36

FIG. 5

| Component | Signal position [ppm] | Integral | Factor | Corrected integral | Ratio [mol%] |
|---|---|---|---|---|---|
| A: MMP | 42.3 | 100.000 | 1 | 100.000 | 81.8 |
| B: MMP hydrate (MMP-OH) | 89.7 | 12.570 | 1 | 12.570 | 10.3 |
| C: Dimers (MMP2O) | 96.6/91.2 | 19.490 | 2 | 9.745 | 7.9 |
|  |  |  |  | 122.315 | 100.0 |

FIG. 6

| | Integral | Factor | Corrected integral | Ratio in mol% | Molar amount (mmol) | Molar mass (g/mol) | Mass (mg) | Content (wt%) |
|---|---|---|---|---|---|---|---|---|
| Tetrachloro-nitrobenzene | 15.680 | 1 | 15.680 | 12.8 | 0.027 | 260.89 | 7.02 | |
| A: MMP | 100.000 | 1 | 100.000 | 81.9 | 0.172 | 104.17 | 17.88 | 82.28 |
| B: MMP hydrate (MMP-OH) | 3.556 | 2 | 1.778 | 1.5 | 0.003 | 122.19 | 0.37 | 1.72 |
| C: Dimers (MMP2O) | 9.395 | 2 | 4.698 | 3.8 | 0.008 | 226.36 | 1.83 | 8.40 |
| | | | 122.156 | 100.0 | | | | 92.40 |

STORAGE-STABLE FORM OF 3-METHYLTHIOPROPIONALDEHYDE

CROSS-REFERENCE TO RELATED APPLICATIONS

The present application is the national stage of international application PCT /EP2019/082083, filed on Nov. 21, 2019, and claims the benefit of the filing date of European Appl. No. 18207569.7, filed on Nov. 21, 2018.

BACKGROUND OF THE INVENTION

Field of the Invention

The present invention relates to a compound of formula (I) having the name 1-(1'-hydroxy-3'-(methylthio)propoxy)-3-(methylthio)propan-1-ol, to a composition comprising said compound and to a process for producing the compound of general formula (I) from 3-methylthiopropionaldehyde (=3-methylmercaptopropionaldehyde, MMP) and water. In addition, the present invention also relates to a process for producing methionine from a compound of general formula (I) or from a composition comprising said compound and to the use of a compound of general formula (I) for the storage and/or transport of 3-methylthiopropionaldehyde.

Description of the Related Art

3-Methylthiopropionaldehyde is an important intermediate in the production of D,L-methionine and the hydroxy analogue thereof 2-hydroxy-4-(methylthio)butyric acid, also known under the abbreviation MHA for methionine hydroxy analogue. 3-Methylthiopropionaldehyde is typically produced by reacting methyl mercaptan with acrolein in a Michael addition. The patents GB 1618884 A, GB 1173174 A and GB 1166961 A disclose methods for the direct production of 3-methylthiopropionaldehyde by reacting methyl mercaptan with acrolein or for the indirect production of 3-methylthiopropionaldehyde, in which 3-methylthiopropionaldehyde is firstly reacted with methyl mercaptan and the reaction product thus obtained is reacted directly with acrolein to give 3-methylthiopropionaldehyde. The documents cited are not concerned with the fact that the 3-methylthiopropionaldehyde obtained has low storage stability, and so no solution to this problem is provided therein.

The problem of the low storage stability of MMP as a result of formation of higher-molecular-weight high boilers (referred to in summary as "residue", since they remain behind as distillation residue during simple distillation) has been known since then. The formation of residue can in this case be attributed primarily to the high reactivity of the α-acidic aldehyde function, which for example promotes intermolecular aldol addition and aldol condensation reactions. Although distilled MMP is usually used in the production in order to avoid introduction of—sometimes also intensely coloured—by-products, intermediate storage and transport between sites mostly takes place by necessity at the markedly more stable stage of undistilled methylmercaptopropionaldehyde. The latter must in turn be admixed with— usually pH-regulating—additives which largely prevent the formation of residue.

In order to make the intermediate MMP used for the synthesis of methionine storage-stable and hence transportable, a very wide variety of additives have to date been added. Examples of additives used include a mixture of triethanolamine and ascorbic acid in WO 93/13059, saturated organic acids that form metal complexes such as L-tartaric acid in EP 899258 A1, N,N-dialkylanilines in JP 49116017 A, iron oxides in JP 10152467 A or amines and organic acids in succession in EP 2813489 A1.

Prior to further use in the process, these additives are removed to a large extent by distillation. Distilled MMP (pure MMP) thus has a significantly reduced storage stability of a few days and is therefore processed further in the production as immediately as possible and in general no longer transported in order to avoid losses due to by-product formation.

It is disadvantageous to the use of additives that these must first be added and subsequently removed again. Considerable effort and costs could be saved were these additions not to be required. In addition, the logistical exchange of intermediates is less flexible because of the limitation of being exclusively able to transport undistilled MMP.

The more recent patent application EP 3205643 A1 avoids the problem of the use of additives by using 1,3-bis(methylthio)propan-1-ol, an addition product of one molecule of MMP and one molecule of methylmercaptan, as a stable storage form for methylmercaptopropionaldehyde and/or methylmercaptan.

Further, EP 3339290 A1 solves the problem of the use of additives by using a composition for the storage and/or transport of 3-methylmercaptopropionaldehyde and/or methylmercaptan, in which MMP is reacted with methylmercaptan to give the storage-stable compound 1-(1,3-bis(methylthio)propoxy)-3-(methylthio)propan-1-ol, an addition product of 2 molecules of MMP and one molecule of methylmercaptan, and also a composition containing this product.

A disadvantage of this storage form as well as the storage form 1,3-bis(methylthio)propan-1-ol from EP 3205643 A1, however, is that these products can not be directly converted further into methionine, but instead the content of methylmercaptan bound therein first of all has to be completely converted beforehand into 3-methylmercaptopropionaldehyde by a further reaction with acrolein, which represents additional effort. At the same time, however, because of the higher risk potential compared to MMP itself, the safety requirements are higher than in the case of storage of MMP.

In contrast, U.S. Pat. No. 4,048,232 firstly describes a process for producing MMP from acrolein and methyl mercaptan with the aid of hexamethylenetetramine as catalyst. In addition, the document mentions that the product thus produced can be directly used further without purification. However, if it is to be stored for a relatively long time, it may be advantageous to treat the product with water and to this end for example to subject the product to a single wash step with 0.01 to 1 part by volume of water, that is to say to bring about a very brief contact with water (column 2, above). However, whether further treatment possibilities exist beyond the washing and, if so, how these might possibly be carried out or which effects might possibly be achieved with them, is not disclosed.

In contrast, WO 03/13059 discloses that the presence of water in an S-substituted aldehyde to be stabilized, such as MMP, must be kept to a minimum, specifically to at most 300 ppm, and preferably to less than 100 ppm (page 22).

EP 899258 A1 [0007] in turn discloses that none of the processes described to date for stabilizing generally alkanals meets the requirement that the stabilization is effected with non-toxic substances at a low dosage and that a water content of up to 2% can be tolerated.

BRIEF SUMMARY OF THE INVENTION

Problem

There was therefore a need for a solution allowing the intermediate 3-methylthiopropionaldehyde to be stored stably as far as possible even in its pure form produced for example by distillation. The use of cost-intensive additives or additives that disrupt later process steps should be able to be largely dispensed with in the process. Stabilization should also be able to be achieved as far as possible without the use of additional hazardous substances, and the stable form should be able to be converted further into methionine as directly as possible.

Solution

It has surprisingly been found that the controlled addition of comparatively small, for example substoichiometric amounts, of water (2.5% to 25% by weight in the resulting mixture) and allowing the mixture to react, without there being substantial removal of water, as would be the case for instance when washing with water, markedly reduces residue formation in distilled MMP. The compound of formula I that is formed here according to the invention and in which two molecules of MMP are masked by one molecule of water apparently brings about this very advantageous effect, also in the inventive composition comprising the compound of formula I, 3-methylthiopropionaldehyde, 3-methylthiopropane-1,1-diol and water. For instance and by way of example, distilled MMP having a water content of 0.14% by weight already exhibited 7.3% by weight of residue after 6 weeks of storage at room temperature, whereas distilled MMP having a water content of 10% by weight only exhibited 0.6% by weight of residue after 6 weeks of storage, that is to say a markedly lower value (cf. Examples 6-9, FIG. 1). In this way, the losses during storage of distilled MMP can be avoided in an extremely simple and very cost-effective way.

The invention therefore provides the use of a chemical compound of formula (I), having the IUPAC name 1-(1'-hydroxy-3'-(methylthio)propoxy)-3-(methylthio)propan-1-ol, which contributes toward solving the problems mentioned above.

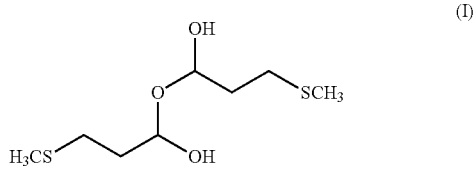

(I)

BRIEF DESCRIPTION OF THE DRAWINGS

The drawings show:
FIG. 5: explanation regarding FIGS. 2 and 3 on the determination of the molar and weight proportions of the composition according to the invention according to $^{13}$C NMR spectra (Relative, molar proportions from $^{13}$C spectrum);
and
FIG. 6: explanation regarding FIGS. 2 and 3 on the determination of the molar and weight proportions of the composition according to the invention according to $^1$H NMR spectra (Content determination (quantitative NMR) $^1$H NMR).

DETAILED DESCRIPTION OF THE INVENTION

Figure 1:
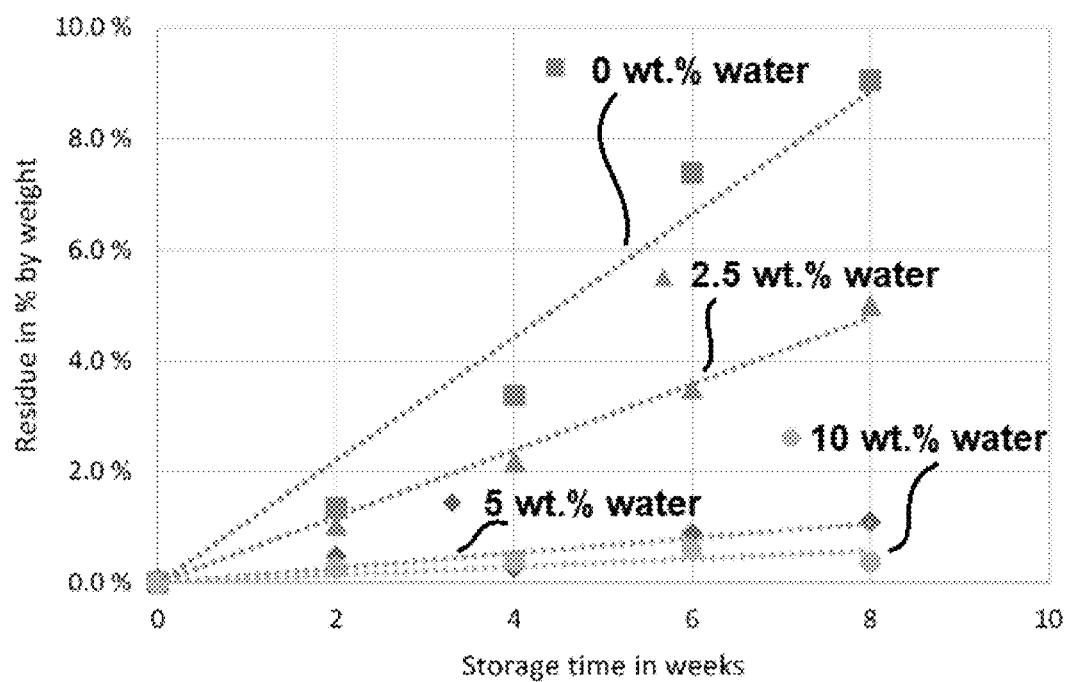
FIG. 1: residue formation trends showing the long-term stability in 3-methylmercaptopropionaldehyde with varying water content (Examples 6-9)

Compound I, which has to date not yet been described, can be can be regarded as dimeric MMP hydrate (MMP$_2$O) and occurs in the form of two diastereomers, with one diastereomer existing as a pair of enantiomers and the second as an achiral meso form, having the following systematic names:
meso-1-(1'-hydroxy-3'-(methylthio)propoxy)-3-(methylthio)propan-1-01,
1-(1'R-1'-hydroxy-3'-(methylthio)propoxy)-3-(methylthio)propan-1S-ol and
1-(1'S-1'-hydroxy-3-(methylthio)propoxy)-3-(methylthio)propan-1R-ol.

Compound I can advantageously be used according to the invention directly in the diastereomer mixture arising due to production-related reasons, but also in diastereomerically or enantiomerically pure form.

The simple MMP hydrate 3-methylthiopropane-1,1-diol can likewise be used as a protected form for the storage and/or transport of 3-methylthiopropionaldehyde. This compound was first described by C. Fernandez-Garcia in Chem. Commun. 2017, 53, 4919. However, to date there has been no indication to its use according to the invention.

The invention therefore primarily provides a composition comprising
40% to 95% by weight of 3-methylthiopropionaldehyde,
1% to 20% by weight of 3-methylthiopropane-1,1-diol,
2% to 25% by weight of a compound of formula I and
2.5% to 25% by weight of water, by means of which the problems mentioned above are solved.

Preference is given here to a composition comprising
40% to 94.5% by weight of 3-methylthiopropionaldehyde,
1% to 20% by weight of 3-methylthiopropane-1,1-diol,
2% to 25% by weight of a compound of formula I and
2.5% to 25% by weight of water.

Very particular preference is given here to a composition comprising
40% to 92% by weight of 3-methylthiopropionaldehyde,
1% to 20% by weight of 3-methylthiopropane-1,1-diol,
2% to 25% by weight of a compound of formula I and
5% to 10% by weight of water.

This composition has proven to be particularly stable and storable, in particular in the temperature range from 0 to 60° C., preferably at 5 to 40° C. A predominantly homogeneous liquid phase exists in this range. This has the particular advantage that the mixture can be introduced directly as an MMP equivalent into the methionine process, without prior homogenization, for example by intensive stirring etc. or even any relatively complex phase separation with downstream separate metering or analysis of the separated phases, being necessary. On the other hand, the proportion of water required, of at most 25% by weight, preferably 10% by weight, is still not large enough that a greatly increased storage volume per MMP equivalent would be necessary as a result. Despite the increase in volume and altered composition, existing MMP storage tanks can as a rule continue to be used, which is highly valuable.

The invention thus also provides for the use of 3-methylthiopropane-1,1-diol or of a compound of formula I or of the composition mentioned above as a protected form for the storage and/or transport of 3-methylthiopropionaldehyde. Storage is preferably effected here in a temperature range from 0 to 60° C., particularly preferably from 5 to 40° C., for a period of time of up to 12 months, preferably up to 8 months, particularly preferably up to 4 months. Under these conditions, residue formation is kept to a low level (compare in particular Examples 8 and 9).

The composition of the type mentioned above can advantageously be produced according to the invention by a process, characterized in that 3-methylthiopropionaldehyde is reacted, while mixing intensively, with 2.5% to 25% by weight of water (based on the total amount of the mixture), preferably 5% to 20% by weight, particularly preferably 5% to 10% by weight of water, at a temperature of 0 to 100° C., preferably at 3 to 70° C., particularly preferably at 5 to 40° C. Intensive mixing of the components is in this context achieved for example with the use of a stirrer at approx. 60-180 rpm.

The preferred duration for the reaction here is 0.5 to 72 h (hours), in particular 1 to 48 h and is selected to be rather shorter at relatively high temperatures, and rather longer at low temperatures.

The enrichment or isolation of the compound of formula I in pure form is in this case advantageously effected by means of chromatography, crystallization or vacuum distillation. Since the compound of formula I exists in temperature-dependent equilibrium with MMP, the MMP hydrate and water, only gentle process variants are advantageously used. Those support materials resulting in a basic to neutral pH should be chosen here as the stationary phase in the chromatography process. The same applies to the eluent, which must not be acidic. For purification by distillation, thin-film evaporator and short path evaporator systems that enable particularly gentle conditions under high vacuum can be considered. For all process variants according to the invention, a pure-MMP quality is preferably used, that is to say a 3-methylthiopropionaldehyde that for example has previously been distilled.

3-Methylthiopropane-1,1-diol, as well as compound I or a composition of the type mentioned above, may be used directly instead of MMP for the production of 2-hydroxy-4-(methylthio)butyronitrile (MMP cyanohydrin), a very industrially important intermediate in the route to methionine or else to methionine hydroxy analogues. This involves reacting the starting materials mentioned with in each case equimolar amounts of hydrocyanic acid, wherein the hydrocyanic acid may also first be released in situ from one of its salts, such as for example from alkali metal cyanide and a proton-donating salt such as, for example, $NH_4Cl$, $NH_4HSO_4$ or $(NH_4)_2SO_4$.

Scheme 1: Formation of MMP hydrates

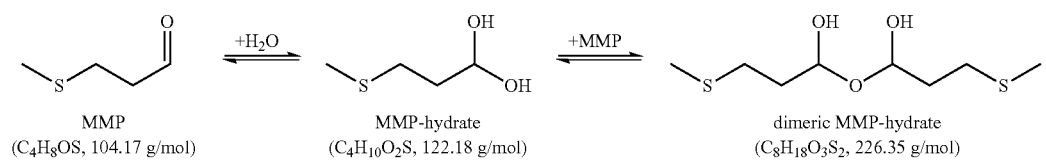

MMP
($C_4H_8OS$, 104.17 g/mol)

MMP-hydrate
($C_4H_{10}O_2S$, 122.18 g/mol)

dimeric MMP-hydrate
($C_8H_{18}O_3S_2$, 226.35 g/mol)

The inventive process is distinguished by the fact that it can be carried out successfully with water and at moderate temperatures in a very simple manner without further auxiliaries. Since water is used in any case in the subsequent production process for methionine, a relatively high water input is not critical in when using the MMP-containing composition according to the invention instead of MMP.

The invention thus also provides the inventive composition comprising 3-methylthiopropionaldehyde, 3-methylthiopropane-1,1-diol, a chemical compound of formula I and water, which has been produced by an inventive method of the type described previously.

The abovementioned inventive process is also very much suitable for the production and enrichment or isolation of the compound with formula I, which is carried out in the manner such that 3-methylthiopropionaldehyde is reacted, while mixing intensively, with 2.5% to 25% by weight of water at a temperature of 0 to 60° C., preferably at 20 to 50° C., very particularly preferably at 25 to 45° C. and compound I is subsequently enriched or isolated. When carrying out the inventive method from technical-grade 3-methylthiopropionaldehyde, a pH of 2.5 to 7 is typically established in the mixture, measured directly using a pH meter with combination electrode. The pH is preferably in the slightly acidic region at pH 3 to 6. It can be precisely adjusted by small additions of organic or inorganic acid or base. This is especially advantageous when the intention is to obtain fairly exact equilibrium proportions of the MMP derivatives mentioned.

3-Methylthiopropane-1,1-diol, as well as compound I or a composition of the type mentioned above, may be used directly instead of MMP for the production of methionine hydantoin, the central intermediate for a commonly used methionine synthesis, the Degussa potassium carbonate cycle process. In this case, reaction is for example effected directly with hydrocyanic acid, ammonia and carbon dioxide or ammonium carbonate/hydrogencarbonate, or via the 2-hydroxy-4-(methylthio)butyronitrile intermediate produced beforehand by reaction with hydrocyanic acid.

Furthermore, 3-methylthiopropane-1,1-diol or compound I or a composition of the type mentioned above are correspondingly usable according to the invention instead of MMP for the production of methionine, for example via the intermediate methionine hydantoin.

The present invention likewise provides for the use of 3-methylthiopropane-1,1-diol or a compound of formula I or a composition of the type mentioned above for the production of the methionine substitute 2-hydroxy-4-(methylthio) butyric acid (MHA), in which the MHA precursor 2-hydroxy-4-(methylthio)butyronitrile is firstly produced therefrom as already stated above. The inventive use can in this way, for example, be integrated into a procedure for the production of MHA as described in EP 143100 B1 (especially Example 1).

The present invention correspondingly also provides a process for producing 2-hydroxy-4-(methylthio)butyronitrile characterized in that 3-methylthiopropane-1,1-diol or a compound according to Claim 1 or an inventive composition stated above is reacted with hydrocyanic acid or other cyanide sources in the presence of an amine base (e.g. triethylamine, pyridine or lutidine) and optionally additionally an acid (buffer). The process parameters can otherwise correspond to those known to the person skilled in the art, for processes proceeding from MMP, from descriptions in the relevant technical literature, such as by way of example in EP 2678313 A1 (especially Examples 1 and 2) or EP 2768312 A1 and also U.S. Pat. No. 5,705,675 (especially Example 4, column 13, from line 29) and the relevant literature respectively cited therein, which are hereby all incorporated by way of reference.

The present invention likewise provides a process for producing methionine hydantoin characterized in that 3-methylthiopropane-1,1-diol or a compound of formula I or a composition of the type described above is reacted in the presence of water with hydrocyanic acid, ammonia and carbon dioxide or ammonium carbonate/hydrogencarbonate or via the intermediate 2-hydroxy-4-(methylthio)butyronitrile produced beforehand by reaction with hydrocyanic acid. The process parameters can otherwise correspond to those known to the person skilled in the art, for processes proceeding from MMP, from descriptions in the relevant technical literature, such as by way of example in EP 780370 A2 (especially Examples 1 to 4) and the relevant literature respectively cited therein, which are hereby all incorporated by way of reference.

Finally, the present invention also provides a corresponding process for producing D,L-methionine by means of reaction of a composition of the type described above with HCN, NH$_3$, carbon dioxide to give methionine hydantoin and subsequent alkaline hydrolysis to give the methionine alkali metal salt and then neutralization with acid to give methionine. The person skilled in the art can also find the process parameters to be used in the relevant technical literature, such as by way of example in EP 780370 A2, which is hereby incorporated by reference, especially Examples 1 to 7.

The corresponding inventive Examples 11 and 12 display high conversions and total yields of methionine, methionine amide and methionylmethionine.

The results relating to this, summarized in Table 4, also make it clear that the MMP$_2$O-rich inventive compositions having a water content ≥2.5% by weight (Examples 11, 12) and the MMP$_2$O-poor, non-inventive compositions having a water content of only approx. 1% by weight (Comparative Examples 1, 2) deliver comparable yields and by-product compositions when producing methionine.

These results also show that the MMP derivatives MMP$_2$O and MMP hydrate, which are present in the inventive composition at proportions of in some cases much greater than 2.5% by weight, can surprisingly be converted under comparable implementation conditions into methionine equivalents in the end product in a manner at least comparable to non-derivatized MMP.

EXAMPLES

Methods Used:

1 Residue Determination by Means of Vacuum Distillation

The residue determination was carried out in a Kugelrohr evaporator of the GKR-50 type from Büchi. For this purpose, the empty weight of the flask used for the distillation was firstly determined. A weight of 15 g of the substance to be distilled (m (initial weight)) was then precisely weighed in and the flask introduced into the Kugelrohr evaporator. The heating of the distillation flask was set to 200° C., and a pressure of 30 mbar was set via the pressure regulator of the vacuum pump. The distillation was carried out on all samples over a period of 20 min. After cooling of the distillation apparatus, the apparatus was vented. The flask was subsequently removed and weighed to determine the weight (m (residue)). The residue was determined using the following formula:

$$\text{Residue [\% by weight]} = \frac{m(\text{residue})}{m(\text{initial weight})}$$

2 NMR Spectroscopic Investigations

The content of the compounds 3-methylthiopropionaldehyde, 3-methylthiopropane-1,1-diol and 1-(1'-hydroxy-3-(methylthio)propoxy)-3-(methylthio)propan-1-ol, present in equilibrium, in a sample was determined by means of NMR spectroscopy (nuclear magnetic resonance) on an Advance 600 type device from Bruker.

For the examples, $^{13}$C NMR spectra of samples to which a solvent had not been added were recorded at 150 MHz. From the recorded spectra, the molar ratios of the constituents to one another were read off. The reference substance used was d$_6$-DMSO, which was introduced in a sealed capillary into the NMR tube of the relevant sample. The ratios were formed by selecting characteristic signals of 3-methylthiopropionaldehyde, 3-methylthiopropane-1,1-diol and 1-(1'-hydroxy-3-(methylthio)propoxy)-3-(methylthio)propan-1-ol in the $^{13}$C NMR spectrum. These were, for 3-methylthiopropionaldehyde, the signal —$\underline{C}$H$_2$—CHO at 42.3 ppm; for 3-methylthiopropane-1,1-diol, the signal —CH$_2$—$\underline{C}$(OH)$_2$ at 89.7 ppm; and for 1-(1'-hydroxy-3-(methylthio)propoxy)-3-(methylthio)propan-1-ol, the signal O($\underline{C}$(OH)—CH$_2$—CH$_2$—SCH$_3$)$_2$ at 91.2 and 96.4 ppm, in this case the sum integral across both diastereomers was formed.

The mass ratios were calculated from the molar ratios taking the total water content, determined by means of Karl Fischer titration, into account.

Figure 2:
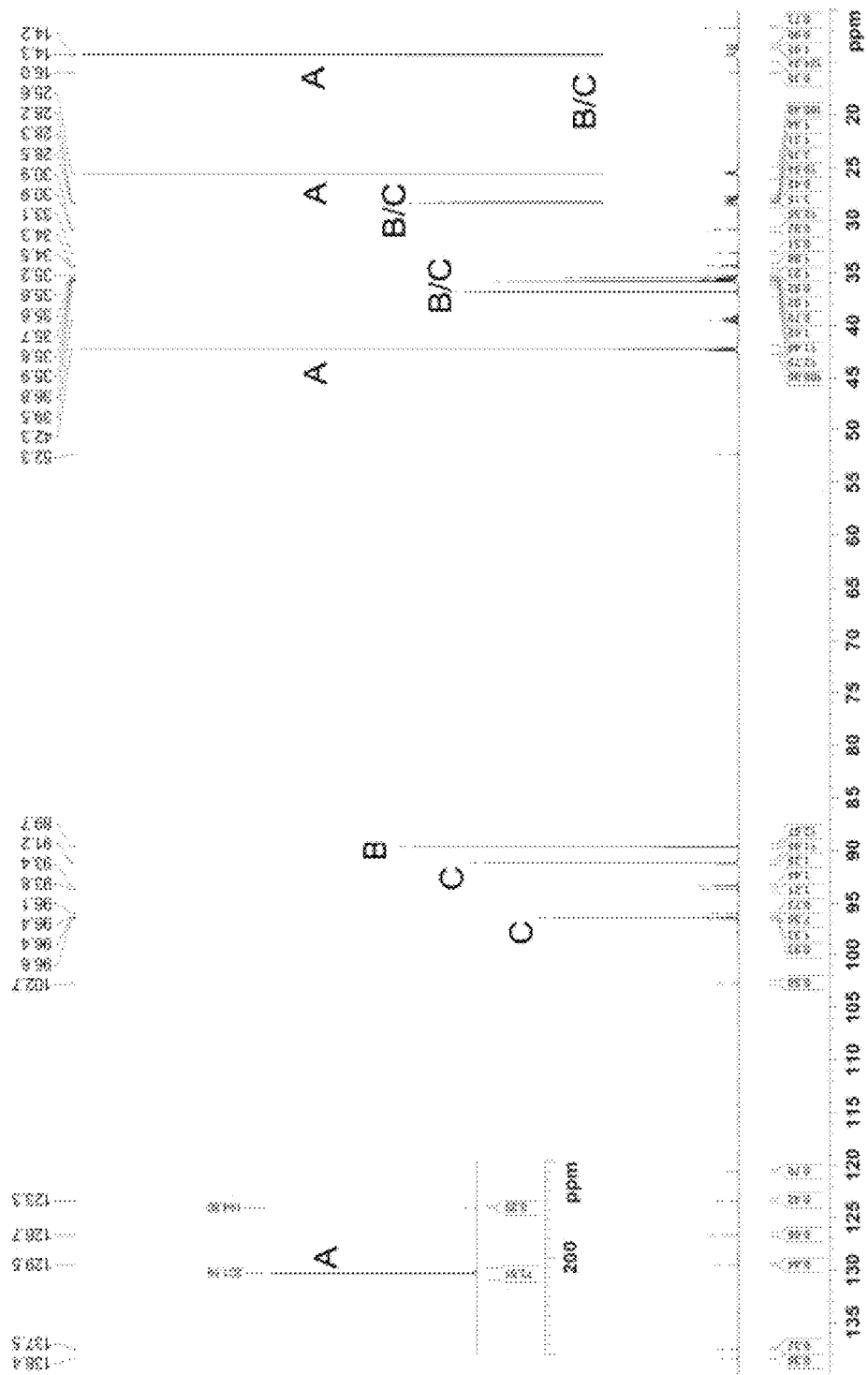
FIG. 2: exemplary $^{13}$C NMR spectrum of a composition according to the invention.
Figure 3:
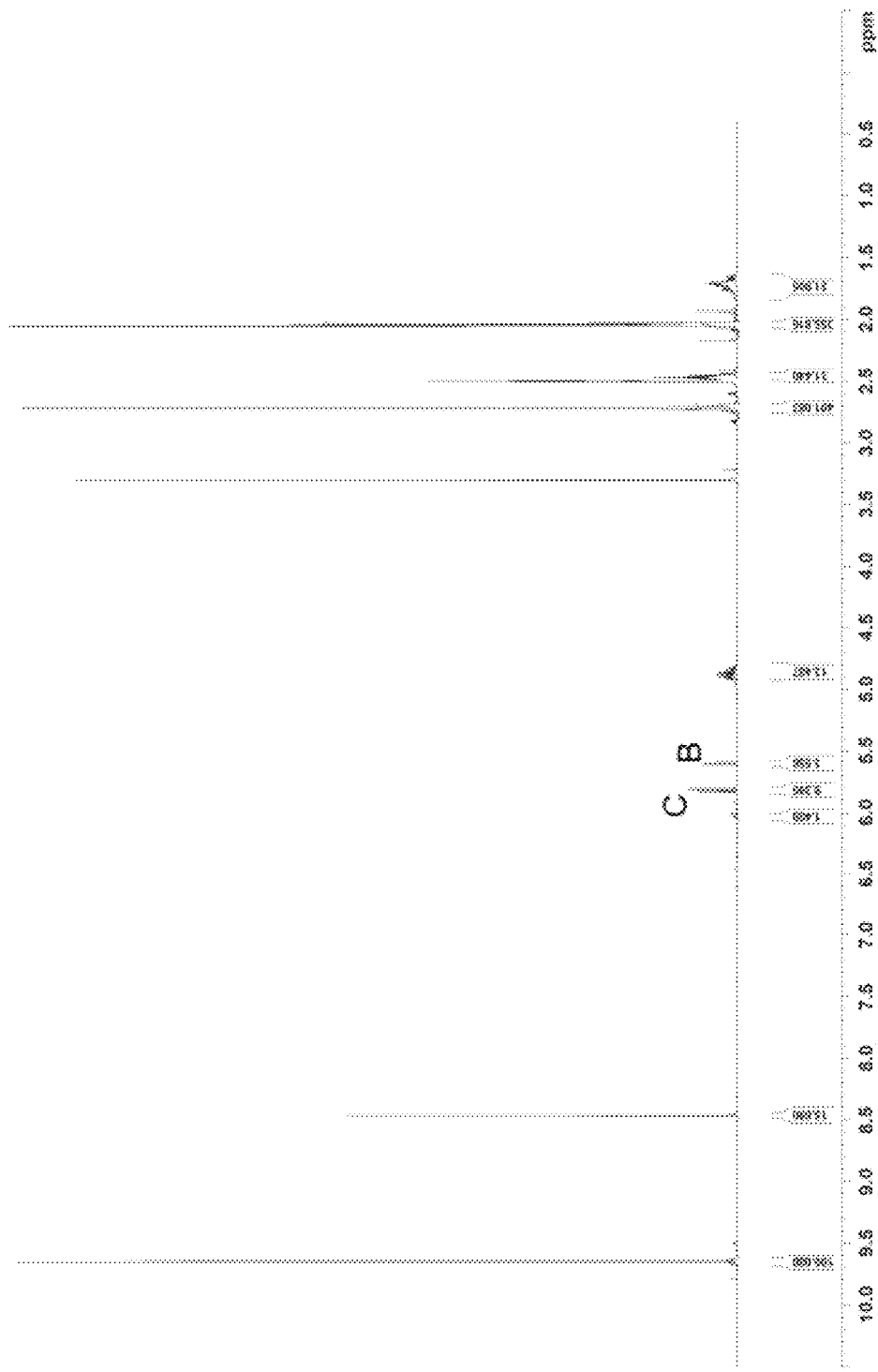
FIG. 3: exemplary $^1$H NMR spectrum of a composition according to the invention.
Figure 4:
FIG. 4: explanations regarding FIGS. 2 and 3 for the purpose of signal assignment.
Figure 4:
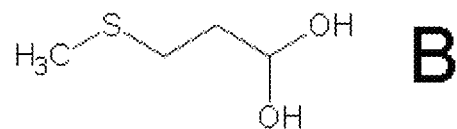
Figure 4:
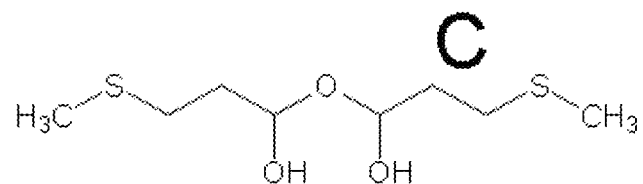

The appended FIGS. 2 and 3 each show an exemplary $^{13}$C NMR (150 MHz, without solvent, de-DMSO capillary) and 1H NMR spectrum (600 MHz, de-DMSO) of an inventive composition.

3 Determination of Water Content by Means of Karl Fischer Titration

The content of water in the inventive compositions was determined by the Karl Fischer method by titration using biamperometric indication of the end point. To this end, 20 to 30 ml of titration medium, e.g. Hydranal Solvent 5 from Fluka, were initially charged in the titration vessel and titrated to dryness with titrant, e.g. Hydranal Titrant 5 from Fluka. An amount of sample of approx. 500 mg was added to the dry-titrated flask using a plastic disposable syringe and titrated with the titrant to the end point. The precise sample weight was determined by differential weighing.

The performance of these standard methods is known to the person skilled in the art and described extensively in the relevant literature, for example, in P. A. Bruttel, R. Schlink, "Wasserbestimmung durch Karl-Fischer-Titration" [Water Determination by Karl Fischer Titration], Metrohm AG, 2006).

4 High Performance Liquid Chromatography (HPLC)

Chromatographic investigations (MMP cyanohydrin, MMP, methionine, methionine amide, hydantoin, hydantoin amide, hydantoic acid, Met-Met) were carried out by means of HPLC from JASCO on an RP-18 column (250×4.6 mm; 5 μm) with subsequent UV detection at 210 nm. A phosphoric acid-acidified acetonitrile-water mixture (3.3 g of $H_3PO_4$, 6.8 g of acetonitrile, 89.9 g of $H_2O$) served as eluent. At a flow rate of 1 ml/min, 10 μl of the respective sample solution (50 mg of sample in 25 ml of $H_2O$) were injected. Calibration was effected in advance by the injection of suitable calibration solutions and evaluation was effected by peak area comparison by means of the external standard method. The procedure of the standard method is known to the person skilled in the art.

Examples 1-2: Preparation of 3-methylthiopropane-1,1-diol (MMP-OH) and of 1-(1'-hydroxy-3'-(methylthio)propoxy)-3-(methylthio)propan-1-ol ($MMP_2O$)

Distilled 3-methylthiopropionaldehyde from industrial production (97.4% by weight; 196.0 g (Example 1), 180.1 g (Example 2)) was initially charged in a flask and admixed with water (4.0 g (Example 1), 20.0 g (Example 2)) while stirring at room temperature. The resulting product mixture was subsequently stirred for 3 days at room temperature and analyzed by means of NMR spectroscopy and Karl Fischer Titration. In Example 1, a content of $MMP_2O$ of 2.9 mol % (corresponding to 6.0% by weight, cf. Tab.1) was ascertained. In Example 2, a content of 7.9 mol %/14.3% by weight was ascertained. The results of Examples 1 and 2 are summarized in Table 1.

admixed with water (30 ml in each case) in a reaction flask with temperature-control jacket. The temperature of the mixture was adjusted (Example 3: 5° C., Example 4: 25° C., Example 5: 40° C.) and the mixture was mixed at this temperature under vigorous stirring (120 rpm) for 15 min. After 15 min the stirrer was switched off, temperature control continued to be maintained. Within a few minutes (Example 5)/a few days (Example 3), two clear, colourless phases formed. The lower organic phase was removed and swiftly characterized by means of HPLC, temperature-controlled NMR spectroscopy and also Karl Fischer titration. The maximum content of $MMP_2O$ was ascertained at 25° C. with approx. 23% by weight (Example 4). The maximum content of MMP-OH within the series of experiments was exhibited by the sample at 5° C.—a content of approx. 15% by weight was ascertained (Example 3). The results of Examples 3 to 5 are summarized in Table 2.

TABLE 2

Overview of Examples 3 to 5 of water-saturated mixtures of the inventive composition at various temperatures

| | | Product composition* | | | |
|---|---|---|---|---|---|
| Example | Temperature | MMP (% by wt.) | MMP-OH (% by wt.) | $MMP_2O$ (% by wt.) | $H_2O$ (% by wt.) |
| 3 | 5° C. | 45.0 | 15.3 | 17.9 | 21.0 |
| 4 | 25° C. | 51.8 | 12.2 | 23.2 | 12.5 |
| 5 | 40° C. | 63.1 | 4.9 | 21.0 | 11.0 |

*determined by calculation by means of HPLC (total content of MMP) and Karl Fischer analysis (total content of $H_2O$) and also $^{13}C$ NMR spectroscopy (molar ratios of MMP:MMP-OH:$MMP_2O$).

TABLE 1

Overview of Examples 1 and 2

| | Reactants | | Product composition | | | | | |
|---|---|---|---|---|---|---|---|---|
| | | | MMP | | MMP-OH | | $MMP_2O$ | $H_2O$ |
| Example | MMP wt./wt. | $H_2O$ | mol %* | % by weight ** | mol %* | % by weight ** | mol %* | % by weight ** | % by weight ** |
| 1 | 98 | 2 | 95.1 | 90.6 | 2.0 | 2.2 | 2.9 | 6.0 | 1.2 |
| 2 | 90 | 10 | 81.8 | 68.2 | 10.3 | 10.1 | 7.9 | 14.3 | 7.4 |

*relative molar ratios from the $^{13}$-C NMR without taking free water into account.
** % by weight calculated taking into account the added water content.

(MMP=3-methylthiopropionaldehyde, MMP-OH=3-methylthiopropane-1,1-diol, $MMP_2O$=1-(1'-hydroxy-3-(methylthio)propoxy)-3-(methylthio)propanol)

Examples 3-5: Investigation of the Equilibrium Position of Monophasic Water-Saturated Mixtures with Inventive Composition Depending on the Temperature Distilled 3-methylthiopropionaldehyde from industrial production (96.1% by weight; 30 ml in each case) was (MMP=3-methylthiopropionaldehyde, MMP-OH=3-methylthiopropane-1,1-diol, $MMP_2O$=1-(1'-hydroxy-3-(methylthio)propoxy)-3-(methylthio)propanol)

Examples 6-9: Storage stability of mixtures containing 1-(1'-hydroxy-3-(methylthio)propoxy)-3-(methylthio)propanol ($MMP_2O$)

Distilled 3-methylthiopropionaldehyde (MMP, 99.8% by weight; water content 0.14% by weight) was admixed with various amounts of water while stirring at room temperature (Example 6: 0.0 g of water for 182.2 g of MMP; Example 7: 4.6 g of water for 179.4 g of MMP; Example 8: 9.4 g of water for 178.6 g of MMP; Example 9: 19.6 g of water for 176.4 g of MMP). The samples were stored at room temperature for a plurality of weeks and the residue was determined at regular intervals by means of vacuum distillation. The results are summarized in Table 3 and also in appended FIG. 1. The results clearly show that a mixture having an increased proportion of $MMP_2O$, such as in particular for Examples 8 and 9, exhibits a markedly reduced residue formation compared to a mixture without $MMP_2O$.

TABLE 3

Overview of Examples 6 to 9

| Example | 6 | 7 | 8 | 9 |
|---|---|---|---|---|
| $H_2O$ in MMP | 0% by wt. | 2.5% by wt. | 5% by wt. | 10% by wt. |
| $MMP_2O$ content* | 0% by wt. | 5% by wt. | 8% by wt. | 15% by wt. |
| Time in weeks | Residue in % by weight | | | |
| 0 | 0.00 | 0.02 | 0.05 | 0.00 |
| 2 | 1.35 | 1.03 | 0.48 | 0.27 |
| 4 | 3.39 | 2.18 | 0.26 | 0.40 |
| 6 | 7.37 | 3.51 | 0.90 | 0.60 |
| 8 | 9.06 | 5.01 | 1.10 | 0.37 |

*estimated values from NMR spectra.

(MMP=3-methylthiopropionaldehyde, $MMP_2O$=1-(1'-hydroxy-3-(methylthio)propoxy)-3-(methylthio)propan-1-ol)

Example 10: Preparation of 2-hydroxy-4-(methylthio)butyronitrile (MMP cyanohydrin) from an inventive composition containing 1-(1'-hydroxy-3-(methylthio)propoxy)-3-(methylthio)propan-1-ol ($MMP_2O$), 3-methylthiopropane-1,1-diol (MMP-OH=MMP hydrate) and MMP 180.1 g of distilled 3-methylthiopropionaldehyde from industrial production (97.4% by weight) were initially charged in a flask and admixed with 20.0 g of water while stirring at room temperature. The product mixture obtained was subsequently stirred for a further 3 days (72 h) at room temperature. Characterization by NMR spectroscopy and Karl Fischer titration yielded a content of 68.2% by weight of 3-methylmercaptopropionaldehyde, 10.1% by weight of MMP-OH and 14.3% by weight of $MMP_2O$ (referred to hereafter as MMP equivalents).

173.6 g of the product mixture (1.50 mol of MMP equivalents) were admixed with catalytic amounts of triethanolamine (58 mg) in a three-neck flask fitted with jacketed coil condenser and dropping funnel, and cooled by means of an ice bath. Cooled hydrocyanic acid (43.48 g, 1.59 mol, 1.06 equiv.) was added over a period of 20 min via the dropping funnel. The dosing was regulated during this so that a temperature of 30° C. was not exceeded. The solution continued to be stirred at room temperature overnight. The colourless, clear product (205.28 g) was characterized by means of HPLC analysis and contained 92.82% by weight of the target compound MMP cyanohydrin (1.45 mol, 96.8% of yield based on MMP equivalents used) and also 1.15% by weight of 3-methylmercaptopropionaldehyde (0.03 mol, 2% by weight) that was in equilibrium with free hydrocyanic acid. The results above show that MMP cyanohydrin can also be produced from water-containing MMP that has been enriched with $MMP_2O$ and MMP-OH, that is to say the inventive composition.

Examples 11-12 with Comparative Examples 1-2: Preparation of methionine via the intermediates 5-[2'-(methylthio)ethyl]imidazolidine-2,4-dione (methionine hydantoin) and MMP cyanohydrin from an inventive composition containing 1-(1'-hydroxy-3-(methylthio)propoxy)-3-(methylthio)propan-1-ol ($MMP_2O$) and MMP 180.1 g of distilled 3-methylthiopropionaldehyde from industrial production (97.4% by weight) were initially charged in a flask and admixed with 20.0 g of water while stirring at room temperature. The product mixture obtained was subsequently stirred for a further 3 days (72 h) at room temperature. Characterization by NMR spectroscopy and Karl Fischer titration yielded a content of 68.2% by weight of 3-methylmercaptopropionaldehyde, 10.1% by weight of MMP-OH, 14.3% by weight of $MMP_2O$ and 7.4% by weight of water.

173.6 g of the product mixture (1.50 mol of MMP equivalents) were admixed with catalytic amounts of triethanolamine (58 mg) in a three-neck flask fitted with jacketed coil condenser and dropping funnel, and cooled by means of an ice bath. Cooled hydrocyanic acid (43.48 g, 1.59 mol, 1.06 equiv.) was added over a period of 20 min via the dropping funnel. The dosing was regulated during this so that a temperature of 30° C. was not exceeded. The solution continued to be stirred at room temperature overnight and the excess of hydrocyanic acid was determined by means of characterization. A further 12.6 g of 3-methylmercaptopropionaldehyde (0.12 mol) were dosed and stirring was continued at room temperature for 20 h in order to adjust the excess of hydrocyanic acid to 0.0 mol %.

37.2 g of the MMP cyanohydrin thus obtained (0.257 mol of MMP equivalents) were admixed with distilled water (35.5 g), ammonium carbonate (13.9 g, 0.15 mol) and ammonium hydrogencarbonate (23.4 g, 0.30 mol) in a 300 ml autoclave beaker equipped with a stirrer bar. The reaction vessel was transferred into a high-pressure laboratory autoclave from ROTH, equipped with manometer, heating system, temperature sensor and pressure relief. The autoclave was tightly sealed, heated within 15 min to 105° C. while stirring and then maintained at this temperature for a further 20 min. At the end of the reaction period, the autoclave was cooled to room temperature under running water and the pressure generated (approx. 15 bar) was released.

41.3 g of aqueous KOH solution (17 g of KOH in 24.3 g of $H_2O$) was then metered in via the inlet tube. After the addition was complete, the autoclave was heated within 25 min to 180° C. while stirring and then maintained at this temperature for a further 40 min. During the reaction period, the pressure was released to 5 bar approx. every 5 min, but at least when 10 bar was exceeded. At the end of the reaction period, the autoclave was cooled to room temperature under running water and depressurized to standard pressure. HPLC analysis of the reaction product (134.7 g) yielded, for a conversion of 97.2%, 60.1% methionine, 6.9% methionine amide and 30.2% methionylmethionine. In a repeat experiment (Example 12), 71.4% methionine, 6.6% methionine amide and 21.4% methionylmethionine were obtained with a conversion of 99.5%.

Comparative Examples 1 and 2

A Comparative Example 1 for the preparation of methionine analogously to Example 11, but using MMP cyanohydrin prepared from MMP$_2$O-poor 3-methylmercaptopropionaldehyde (containing 1.2% by weight of water) according to Example 1, yielded, with a conversion of 95.0%, 63.0% methionine, 5.5% methionine amide and 26.5% methionylmethionine; in a repeat experiment (Comparative Example 2), 65.8% methionine, 6.5% methionine amide and 24.2% methionylmethionine were obtained with a conversion of 96.5%.

TABLE 4

Comparison of methionine preparation from MMP$_2$O-rich and MMP$_2$O-poor inventive composition containing MMP

| | Reactant composition, % by weight MMP$_2$O (MMP, MMP-OH, H$_2$O) | Conversion, % Methionine (Met-amide; Met-Met) |
|---|---|---|
| Example 11 | 14.3 (68.2; 10.1; 7.4) | 60.1 (6.9; 30.2) |
| Example 12 | | 71.4 (6.6; 21.4) |
| Comparative example 1 | 6.0 (90.6; 2.2; 1.2) | 63.0 (5.5; 26.5) |
| Comparative example 2 | | 65.8 (6.5; 24.2) |

(MMP=3-methylthiopropionaldehyde, MMP-OH=3-methylthiopropane-1,1-diol, MMP$_2$O=1-(1'-hydroxy-3-(methylthio)propoxy)-3-(methylthio)propan-1-ol)

The results summarized in Table 4 show that MMP$_2$O-rich inventive compositions (Examples 11, 12) and MMP$_2$O-poor inventive compositions (Comparative Examples 1, 2) deliver comparable yields and by-product spectra in the preparation of methionine, and so MMP$_2$O (1-(1'-hydroxy-3-(methylthio)propoxy)-3-(methylthio)propan-1-ol) and also MMP-OH (3-methylthiopropane-1,1-diol) can clearly also be converted to methionine via MMP cyanohydrin and methionine hydantoin. The relatively high proportions of Met-Met of above 20% can in this case be attributed to the execution in the laboratory, and are in the low percentage region in continuous industrial hydrolysis columns in the methionine process.

The invention claimed is:

1. A composition, comprising:
   3 methylthiopropionaldehyde, in a range of from 40 to 95 wt. %;
   3 methylthiopropane-1,1-diol, in a range of from 1 to 20 wt. %;
   a compound of formula (I), in a range of from 2 to 25 wt. %;

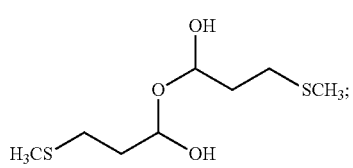

(I)

and
   water, in a range of from 2.5 to 25 wt. %.

2. The composition of claim 1, comprising:
   the 3-methylthiopropionaldehyde, in a range of from 40 to 94.5 wt. %.

3. The composition of claim 1, comprising:
   the 3-methylthiopropionaldehyde, in a range of from 40 to 92 wt. %; and
   the water, in a range of from 5 to 10 wt. %.

4. A method of storing and/or transporting 3-methylthiopropionaldehyde, the method comprising:
   contacting the composition of claim 1, 3-methylthiopropane-1,1-diol, or the compound of formula (I), with the 3-methylthiopropionaldehyde.

5. The method of claim 4, conducted at a temperature in a range of from 0 to 60° C., for a period of time of up to 12 months.

6. The method of claim 5, conducted at a temperature in a range of from 5 to 40° C.

7. The method of claim 5, conducted for a period of time of up to 8 months.

8. The method of claim 5, conducted for a period of time of up to 4 months.

9. A method for producing the composition of claim 1, the method comprising:
   reacting 3-methylthiopropionaldehyde, while mixing intensively, with 2.5 to 25 wt. % of water, based on a total amount of the 3-methylthiopropionaldehyde and water used, at a temperature in a range of from 0 to 100° C.

10. The method of claim 9, wherein the reaction is conducted for a duration in a range of from 0.5 to 72 h.

11. The method of claim 9, further comprising:
   distilling the 3-methylthiopropionaldehyde before the reacting.

12. A method for producing 2-hydroxy-4-(methylthio)butyronitrile, the method comprising:
   reacting the composition of claim 1, 3-methylthiopropane-1,1-diol, or the compound of formula (I), with hydrocyanic acid in the presence of an amine base.

13. A method for producing methionine hydantoin, the method comprising:
   reacting the composition of claim 1, 3-methylthiopropane-1,1-diol or the compound of formula (I), in the presence of water with hydrocyanic acid, ammonia, and carbon dioxide.

14. A method for producing D,L-methionine the method comprising:
   reacting the composition of claim 1 with HCN, NH$_3$, and carbon dioxide to give methionine hydantoin; and subsequently
   hydrolyzing the methionine hydantoin, under alkaline conditions, to give a methionine alkali metal salt; and then
   neutralizing the methionine alkali metal salt with acid to give methionine.

15. The composition of claim 1, produced by a method comprising:
    reacting 3-methylthiopropionaldehyde, while mixing intensively, with 2.5 to 25 wt. % of water, based on a total amount of the 3-methylthiopropionaldehyde and water used, at a temperature in a range of from 0 to 100° C.

16. A method of producing 2-hydroxy-4-(methylthio) butyric acid, the method comprising:
    producing 2-hydroxy-4-(methylthio)butyronitrile by the method of claim 12; and
    hydrolyzing the 2-hydroxy-4-(methylthio)butyronitrile in the presence of aqueous sulfuric acid to form a mixture comprising the 2-hydroxy-4-(methylthio)butyric acid and ammonium hydrogen sulfate.

* * * * *